United States Patent [19]
Oppong et al.

[11] Patent Number: 5,929,073
[45] Date of Patent: Jul. 27, 1999

[54] SYNERGISTIC ANTIMICROBIAL COMPOSITIONS CONTAINING DODECYLMORPHOLINE A SALT THEREOF AND DODECYLAMINE OR A SALT THEREOF

[75] Inventors: David Oppong, Cordova; Percy A. Jaquess, Tigrett; Fernando Del Corral, Memphis; Marilyn S. Whittemore, Germantown, all of Tenn.

[73] Assignee: Buckman Laboratories International, Inc., Memphis, Tenn.

[21] Appl. No.: 08/931,442

[22] Filed: Sep. 16, 1997

[51] Int. Cl.$^6$ .......................... A01N 33/00; A01N 33/02; A01N 43/34; A61K 31/535
[52] U.S. Cl. ...................... 514/231.2; 504/155; 504/158; 514/556; 514/663
[58] Field of Search .................................... 504/155, 158; 514/231.2, 556, 663

[56] References Cited

U.S. PATENT DOCUMENTS

| | | | |
|---|---|---|---|
| 3,140,976 | 7/1964 | Berenschot et al. | 167/22 |
| 4,179,469 | 12/1979 | Imai | 260/577 |
| 5,086,048 | 2/1992 | Brandes et al. | 514/187 |
| 5,250,194 | 10/1993 | Hollis et al. | 210/764 |
| 5,322,834 | 6/1994 | Hsu | 504/156 |
| 5,693,631 | 12/1997 | Whittemore et al. | 514/183 |

FOREIGN PATENT DOCUMENTS

| | | |
|---|---|---|
| 646207 | 11/1950 | United Kingdom . |
| 1202041 | 8/1970 | United Kingdom . |
| WO 96/38043 | 5/1996 | WIPO . |
| WO 97/28687 | 8/1997 | WIPO . |

*Primary Examiner*—Allen J. Robinson
*Attorney, Agent, or Firm*—Armstrong, Westerman, Hattori, McLeland & Naughton

[57] ABSTRACT

Compositions for controlling the growth of microorganisms in or on a product, material, or medium comprising synergistically effective amounts of (a) dodecylmorpholine or a salt thereof and (b) dodecylamine or a salt thereof are disclosed. Methods to control the growth of microorganisms and prevent spoilage caused by microorganisms with the use of the compositions of the present invention are also disclosed.

28 Claims, No Drawings

SYNERGISTIC ANTIMICROBIAL COMPOSITIONS CONTAINING DODECYLMORPHOLINE A SALT THEREOF AND DODECYLAMINE OR A SALT THEREOF

FIELD OF INVENTION

The present invention relates to certain compositions and processes useful for controlling the growth of one or more microorganisms and for preventing spoilage caused by one or more microorganisms in various products, materials, or medium, particularly, in industrial products, materials, or media. These products, materials or media include, but are not limited to, wood pulp, wood chips, lumber, adhesives, coatings, animal hides, paper mill liquors, process waters, pharmaceutical formulations, cosmetic and toiletry formulations, geological drilling lubricants, petrochemicals, agrochemical compositions, paints, leathers, wood, metalworking fluids, cooling water (e.g., cooling tower water), tanning liquors, starch, proteinaceous materials, acrylic latex paint emulsions, textiles, influent water, recreational water, waste water, pasteurizers, retort cookers, and lithographic fountain solutions.

The novel compositions and processes incorporating the compositions of the present invention are processes or mixtures which show unexpected, synergistic activity against microorganisms, including bacteria, fungi, algae, or mixtures thereof. Specifically, the present invention is directed to the use of compositions containing a mixture of a) dodecylmorpholine or salts thereof and b) dodecylamine or salts thereof.

BACKGROUND OF THE INVENTION

Many of the products, materials, or media referred to above when wet or subjected to treatment in water are susceptible to deterioration or degradation including degradation by bacteria, fungi, algae, or mixtures thereof, unless steps are taken to inhibit such degradation or deterioration.

To control deterioration or degradation caused by microorganisms, many types of industrial microbicides are used but some of these biocides are of questionable utility because they have undesirable odors, are high in cost, show low degree of effectiveness, or create hazards with respect to storage, use, or handling.

For instance, the use of such popular industrial microbicides as organomercury compounds, organotin compounds, and chlorinated phenols have come under great regulatory pressure in recent times because of their high toxicity and concern about their adverse effects on the environment. Consequently, workers in the trade have continued to seek improved biocides that have low toxicity and are capable of exhibiting a prolonged biocidal effect at normal use levels.

Accordingly, the present invention is directed to microbicidal compositions and processes that substantially obviate one or more of the problems, limitations, and disadvantages described above and experienced by those working in this art. In particular, the compositions of the present invention are capable of controlling the growth of at least one microorganism, especially fungi, bacteria, algae, or mixtures thereof, preferably over prolonged periods of time. Preferably, the compositions are also safe and economical to use. The present invention is also directed to methods or processes of controlling the growth of at least one microorganism.

SUMMARY OF THE INVENTION

Accordingly, it is an object of the present invention to provide a microbicidal composition capable of controlling the growth of at least one microorganism, particularly, fungi, bacteria, algae, or mixtures thereof, preferably over prolonged periods of time.

It is an additional object to provide such compositions which are economical to use. Methods of controlling the growth of at least one microorganism are also objects of this invention.

The present invention provides a composition to control the growth of at least one microorganism comprising a mixture of (a) dodecylmorpholine or a salt thereof and (b) dodecylamine or a salt thereof where the components are present in a combined amount synergistically effective to control the growth of at least one microorganism. The composition preferably provides superior microbicidal activity at low concentrations against a wide range of microorganisms. This composition can also be considered a surface active agent that has the ability to control the growth of at least one microorganism.

The present invention also provides a method for controlling the growth of at least one microorganism in or on a material or medium susceptible to attack by the microorganism which comprises the step of contacting the microorganism with the composition of the present invention or including the composition of the present invention in a product susceptible to microbial attack, where the components of the composition are present in synergistically effective amounts to control the growth of the microorganism. The synergistically effective amount varies in accordance with the product, material, or media to be treated and can, for a particular application, be routinely determined without undue experimentation, by one skilled in the art in view of this disclosure.

The present invention also embodies the separate addition of a mixture of (a) dodecylmorpholine or a salt thereof and (b) dodecylamine or a salt thereof. According to this embodiment, the components are individually added to the system so that the final amount of the mixture of (a) dodecylmorpholine or a salt thereof and (b) dodecylamine or a salt thereof present in the system at the time of use is that amount synergistically effective to control the growth of at least one microorganism.

The compositions of the present invention can be useful in preserving various types of industrial products, media, or materials susceptible to the attack by microorganisms. Such products, media, or materials include, but are not limited to, dyes, pastes, lumber, leathers, textiles, pulp, wood chips, tanning liquors, paper mill liquors, polymer emulsions, paints, paper and other coating and sizing agents, petrochemicals, metalworking fluids, geological drilling lubricants, cooling water systems, pharmaceutical formulations, and cosmetic and toiletry formulations.

The compositions can also be useful in agrochemical formulations for the purpose of protecting seeds or crops against microbial spoilage.

Additional advantages of the present invention will be set forth in part in the description which follows, and in part will be apparent from the description, or may be learned by the practice of the present invention. The advantages of the present invention may be realized and obtained by means of the elements and combinations particularly pointed out in the claims.

It is to be understood that both the foregoing general description and the following detailed description are exemplary and explanatory only and are not restrictive of the present invention, as claimed.

DETAILED DESCRIPTION OF THE PRESENT INVENTION

According to the methods of the present invention, controlling or inhibiting the growth of at least microorganism includes both the reduction and/or the prevention of such growth.

It is to be further understood that "controlling" the growth of at least one microorganism can include inhibiting the growth of a microorganism (i.e., there is no growth or essentially no growth of the microorganism). "Controlling" the growth of at least one microorganism can also include maintaining the microorganism population at a desired level and/or reducing the population to a desired level (even to undetectable limits, e.g., zero population). Thus, the products, material, or mediums susceptible to attack by these tppes of microorganisms can be preserved from this attack and the resulting spoilage and other detrimental effects caused by the microorganism can be minimized or avoided. Furthermore, it is also to be understood that "controlling" the growth of at least one microorganism can also include biostatically reducing and/or maintaining a low level microorganism such that the attack by a microorganism and any resulting spoilage or other detrimental effects are mitigated, e.g., the microorganism growth rate or microorganism attack rate is slowed down or eliminated.

When two chemical microbicides are combined or mixed into one product or added separately, three results are possible:

1) The chemicals in the product produce an additive (neutral) effect;
2) The chemicals in the product produce an antagonistic effect; or
3) The chemicals in the product produce a synergistic effect.

An additive effect has no economic advantage over the individual components. The antagonistic effect would produce a negative impact. Only a synergistic effect, which is less likely than either an additive or antagonistic effect, would produce a positive effect and therefore be of economic advantage.

It is well-known in the microbicidal literature that there is no theoretical method to provide the likelihood of knowing, before actually testing, whether additive, antagonistic, or synergistic effects will be obtained when two biocides are mixed to yield a formulation.

The microbicidal compositions of the prevention invention are mixtures of a) dodecylmorpholine or a salt thereof and b) dodecylamine or a salt thereof and demonstrate an unexpected synergistic effect compared to the respective components alone, and thus achieve superior, i.e., greater than additive, microbicidal activity preferably at low concentrations, against a wide variety of microorganisms.

The dodecylmorpholine has the formula:

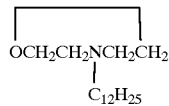

The dodecyl alkyl group is perferably linear on both the dodecylomorpholine and dodecylamine. A preferred salt of dodecylmorpholine is

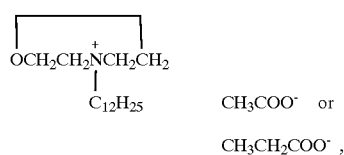

where dodecylmorpholine acetate is the most preferred salt. Other preferred examples of salts include a lauric acid salt of dodecylmorpholine and a neodecanoic salt of dodecylmorpholine. Similarly, preferred salts of dodecylamine are $N^+H_2(C_{12}H_{25})(CH_3COO)^-$ or $N^+H_2(C_{12}H_{25})(CH_3CH_2COO)^-$, with dodecylamine acetate being the most preferred salt of dodecylamine. Other preferred examples of salts include a lauric acid salt of dodecylamine and a neodecanoic salt of dodecylamine.

More than one type of dodecylmorpholine or salts thereof and/or more than one type of dodecylamine or salts thereof can be used to form the mixtures or compositions of the present invention.

Examples of microorganisms controllable by the compositions of the present invention include fungi, bacteria, algae, and mixtures thereof such as *Pseudomonas aeruginosa, Enterobacter aerogenes*, Chlorella Sp., *Aspergillus niger*. These organisms are some of the most common organisms associated with spoilage of products, materials, or media. Since these organisms can be some of the toughest organisms to control, the compositions of the present invention are believed to be effective against most bacteria, fungi, algae, or mixtures thereof. Preferably, the compositions of the present invention have a low toxicity.

The compositions of the present invention can also be considered surface active agents which can suspend microorganisms in such a state that reproduction is substantially prevented.

The components of the compositions of the present invention are commercially available and can easily be synthesized from commercially available raw materials. Also, the preparation of dodecylmorpholine and salts thereof are described in U.S. Pat. No. 5,250,194, which is fully incorporated by reference herein.

The components of the compositions of the present invention may be chosen based on the compatibility of these components with the products, materials, or media. Compatibility may be determined by criteria such as solubility in the fluid system and/or lack of reactivity with the fluid, material, or media in question. The compatibility is readily determined by one of ordinary skill in the art by adding the compositions of the present invention to the product, material, or media to be used. When used in a fluid system it is preferable that the composition be freely soluble in the particular fluid resulting in a uniform solution or dispersion.

In the following discussion of preferred embodiments, component (a) is dodecylmorpholine or a salt thereof and component (b) is dodecylamine or a salt thereof.

As described above, components (a) and (b) are used in synergistically effective amounts. The weight ratios of (a) to (b) vary depending on the type of microorganisms, products, materials, or media to which the composition is applied. One skilled in the art can readily determine without undue experimentation, the appropriate weight ratios for a specific application. The ratio of component (a) to component (b) preferably ranges from about 1:99 to about 99:1, more preferably from about 1:30 to about 30:1, and most preferably from about 1:5 to about 5:1.

In general, an effective fungicidal, bactericidal, and algicidal response can be obtained when the synergistic combination is employed in concentrations ranging from about 0.01 to about 5000 ppm of dodecylmorpholine or a salt thereof, preferably from about 0.1 to about 2000 ppm, and most preferably from about 0.1 to about 1000 ppm; and from about 0.01 to about 5000 ppm of dodecylamine or a salt thereof, preferably from about 0.1 to about 2000 ppm, and most preferably from about 0.1 to about 1000 ppm.

In accordance with the present invention, the composition of the present invention may be in the form of a solid, dispersion, emulsion, or solution, depending upon the particular application. Further, the components of the composition may be applied separately or may be combined first and then applied to the product, material, or medium.

The present invention also provides a method for controlling the growth of at least one microorganism in or on a product, material, or medium susceptible to attack by the microorganism which comprises the step of adding to the product, material, or medium, a composition of the present invention, where the components of the composition are present in synergistically effective amounts. Furthermore, the present invention provides a method of preventing spoilage of a product, material, or medium caused by a microorganism, comprising the step of applying to the product, material or medium, a composition of the present invention where the components of a composition are present in synergistically effective amounts. For example, the composition may be used to prevent the spoilage of seeds or crops, e.g., cotton, barley, rice, maize, tobacco, etc.

Depending upon the intended use, the mode as well as the rate of application of the composition of this invention could vary. For instance, the composition could be applied by a device spraying or brushing onto the material or product. The material or product in question could also be treated by dipping in a suitable formulation of the composition. In a liquid or liquid-like medium, the composition could be added into the medium by pouring or by metering with a suitable device so that a solution or a dispersion of the composition could be produced. If used as a liquid preservative, for example, the composition may be prepared as an aqueous emulsion. If necessary or desirable, a surfactant may be added to the composition.

Based on this specific application, the composition may be prepared in liquid form by dissolving the composition in organic solvent. The compositions of the present invention may be prepared in an emulsion form by emulsifying the composition in water, or if necessary, by adding a surfactant. In accordance with the present invention, additional components such as insecticides and the like may be added to the foregoing preparations without affecting the synergistic effects of the composition. Insecticides that may be used include, but are not limited to, pyrethrins, nicotine, chlordane, and parathions.

The synergistic activity of the combinations described above has been confirmed using standard laboratory techniques as illustrated below. The following examples are intended to illustrate, not limit, the present invention.

Microbiological Evaluation

A. Fungal Evaluation

Mineral salts-glucose medium was used. To prepare the medium, the following ingredients were added to 1 liter of deionized water: 0.7 g of $KH_2PO_4$, 0.7 g of $MgSO_4.7H_2O$, 1.0 g of $NH_4NO_3$, 0.005 g NaCl, 0.002 g $FeSO_4.7H_2O$, 0.002 g of $ZnSO_4.7H_2O$, 0.001 g $MnSO_4.7H_2O$, and 10 g of glucose. The pH of the medium was adjusted to 6 with 1N NaOH. The medium was distributed in 5 ml amounts in test tubes and autoclaved at 121° C. for 20 minutes. The fungus, Aspergillus niger, was grown on a potato dextrose agar slant for 7 to 10 days and a spore suspension prepared by washing down the spores from the slant into a sterile saline solution. After addition of the biocides in the desired concentrations to the sterile mineral salts-glucose medium, the fungal spore suspension was added. The final spore concentration was approximately $10^6$ cfu/mL. the inoculated media was incubated at 28° C. for 14 days.

B. Bacterial Evaluation

Nutrient broth (2.5 g/liter of deionized water) was prepared. This was distributed in 5 mL amounts into test tubes and autoclaved for 20 minutes at 121° C. After addition to the biocides in the desired concentrations to the nutrient broth, 100 microliters of a suspension of Pseudomonas aeruginosa or Enterobacter aerogenes cells of approximately $9.3 \times 10^8$ cfc/mL were added and incubated at 37° C. for 24 or 48 hours.

C. Algae Test

An algae broth was prepared by dissolving the following ingredients in 1 liter of deionized water: 1.0 g of $NaNO_3$, 50 mg of $NH_4Cl$, 58 mg of $CaCl_2$, 0.513 g of $MgSO_4$, 0.25 g $K_2HPO_4$, and 3.0 mg of $FeCl_3.6H_2O$. The medium was distributed in 50 ml amounts into flasks and autoclaved at 121° C. for 20 minutes. After autoclaving, the biocides were added to the broth in the desired concentrations. Then one milliliter of a two-week old culture of a Chlorella sp. was added and incubated at a temperature of 25–28° C. and lighting of 180 ft.-candle intensity (12 hours light; 12 hours darkness) for 14 days.

In the examples 1 through 3, synergism was demonstrated in separate experiments by testing dodecylmorpholine or dodecylmorpholine acetate designated as component A and dodecylamine or dodecylamine acetate as component B in a series of tests in varying ratios and a range of concentrations against the fungus Aspergillus niger, the bacteria Pseudomonas aeruginosa or Enterobacter aerogenes, and the alga Chlorella sp. using the methods described above.

The lowest concentration of each mixture of compound which completely prevented growth of the bacteria for 24 hours or 48 hours, fungus or algae for two weeks was taken as the end points for synergism calculations. End points for the various mixtures were then compared with the end points for the pure active ingredients alone in concomitantly prepared flasks or test tubes.

Synergism was demonstrated by the method described by Kull, E. C., Eisman, P. C., Sylwestrwicz, H. D., and Mayer, R. L., 1961, Applied Microbiology, 9:538–541, wherein:

$$QA/Qa + QB/Qb \text{ is less than 1}$$

Qa=Concentration of compound A in parts per million, acting alone, which produced an end point.

Qb=Concentration of compound B in parts per million, acting alone, which produced an end point.

QA=Concentration of compound A in parts per million, in the mixture, which produced an end point.

QB=Concentration of compound B in parts per million, in the mixture, which produced an end point.

When the sum of QA/Qa and QB/Qb is greater than one, antagonism is indicated and when the sum is equal to one, additivity is indicated. When the sum of this value is less than one, synergism exists.

This procedure for demonstrating synergism of the compositions of this invention is a widely used and acceptable procedure. More detailed information is provided in the article by Kull et al. Further information concerning this procedure is contained in U.S. Pat. No. 3,231,509, which disclosure is hereby made part of this application.

Based on the above criteria, a synergistic activity against bacteria, fungi, and algae is observed when dodecylmorpholine or dodecylmorpholine acetate is combined with dodecylamine or dodecylamine acetate. Examples showing synergistic results can be found in Examples 1–4.

It will be apparent for those skilled in the art that the required synergistically effective amounts (concentrations) will vary depending on the particular organisms and particular applications, and can readily be determined by routine experimentation. Use of a synergistically effective amount enables the use of substantially smaller amounts of (a) the dodecylmorpholine or a salt thereof or (b) dodecylamine or a salt thereof to achieve a given effect then would be necessary for each parasite if used alone or then would be necessary if a mere additive effect from these two biocides were obtained.

It will be apparent to those skilled in the art that various modifications and variations can be made in the compositions and methods of the present invention without departing from the spirit or scope of the invention. Thus, it is intended that the present invention cover the modifications and variations of this invention provided that they come within the scope of the appended claims and their equivalents.

EXAMPLE 1

Component A = Dodecylmorpholine
Component B = Dodecylamine

Quantities producing end points (ppm)

| Test organism | $Q_a$ | $Q_A$ | $Q_b$ | $Q_B$ | $Q_A/Q_a$ | $Q_B/Q_b$ | $Q_A/A_a$ + $Q_B/Q_b$ |
|---|---|---|---|---|---|---|---|
| Enterobacter aerogenes | 60 | — | — | — | — | — | — |
| | — | 30 | — | 10 | 0.5 | 0.4 | 0.9 |
| | — | 15 | — | 10 | 0.25 | 0.4 | 0.65 |
| | — | 6 | — | 10 | 0.1 | 0.4 | 0.5 |
| | — | 3 | — | 10 | 0.05 | 0.4 | 0.45 |
| | — | 1.5 | — | 10 | 0.03 | 0.4 | 0.43 |
| | — | 0.6 | — | 10 | 0.01 | 0.4 | 0.41 |
| | — | 30 | — | 5 | 0.5 | 0.2 | 0.7 |
| | — | 15 | — | 5 | 0.25 | 0.2 | 0.45 |
| | — | 6 | — | 5 | 0.1 | 0.2 | 0.3 |
| | — | 30 | — | 2.5 | 0.5 | 0.1 | 0.6 |
| | — | 15 | — | 2.5 | 0.25 | 0.1 | 0.35 |
| | — | — | 25 | — | — | — | — |

EXAMPLE 2

Component A = Dodecylmorpholine
Component B = Dodecylamine

Quantities producing end points (ppm)

| Test organism | $Q_a$ | $Q_A$ | $Q_b$ | $Q_B$ | $Q_A/Q_a$ | $Q_B/Q_b$ | $Q_A/A_a$ + $Q_B/Q_b$ |
|---|---|---|---|---|---|---|---|
| Aspergillus niger | 150 | — | — | — | — | — | — |
| | — | 60 | — | 25 | 0.4 | 0.5 | 0.9 |
| | — | 60 | — | 10 | 0.4 | 0.2 | 0.6 |
| | — | 30 | — | 25 | 0.2 | 0.5 | 0.7 |
| | — | 30 | — | 10 | 0.2 | 0.2 | 0.4 |
| | — | 15 | — | 25 | 0.1 | 0.5 | 0.6 |
| | — | 6 | — | 25 | 0.04 | 0.5 | 0.54 |
| | — | 3 | — | 25 | 0.02 | 0.5 | 0.52 |
| | — | 1.5 | — | 25 | 0.01 | 0.5 | 0.51 |
| | — | — | 50 | — | — | — | — |

EXAMPLE 3

Component A = Dodecylmorpholine
Component B = Dodecylamine

Quantities producing end points (ppm)

| Test organism | $Q_a$ | $Q_A$ | $Q_b$ | $Q_B$ | $Q_A/Q_a$ | $Q_B/Q_b$ | $Q_A/A_a$ + $Q_B/Q_b$ |
|---|---|---|---|---|---|---|---|
| Chlorella sp. | 1.5 | — | — | — | — | — | — |
| | — | 0.6 | — | 0.25 | 0.4 | 0.5 | 0.9 |
| | — | 0.3 | — | 0.25 | 0.2 | 0.5 | 0.7 |
| | — | 0.6 | — | 0.1 | 0.4 | 0.2 | 0.6 |
| | — | 0.4 | — | 0.2 | 0.27 | 0.4 | 0.67 |
| | — | 0.3 | — | 0.2 | 0.2 | 0.4 | 0.6 |
| | — | 0.24 | — | 0.2 | 0.16 | 0.4 | 0.56 |
| | — | — | 0.5 | — | — | — | — |

EXAMPLE 4

Component A = Dodecylmorpholine
Component B = Dodecylamine acetate

Quantities producing end points (ppm)

| Test organism | $Q_a$ | $Q_A$ | $Q_b$ | $Q_B$ | $Q_A/Q_a$ | $Q_B/Q_b$ | $Q_A/A_a$ + $Q_B/Q_b$ |
|---|---|---|---|---|---|---|---|
| Pseudomonas aeruginosa | >100 | — | — | — | — | — | — |
| | — | 100 | — | 10 | <1 | 0.4 | 1.4 |
| | — | 50 | — | 10 | 0.5 | 0.4 | 0.9 |
| | — | 25 | — | 10 | 025 | 0.4 | 0.65 |
| | — | 10 | — | 10 | 0.1 | 0.4 | 0.5 |
| | — | 5 | — | 10 | 0.05 | 0.4 | 0.45 |
| | — | 2.5 | — | 10 | 0.03 | 0.4 | 0.43 |
| | — | 1 | — | 10 | 0.01 | 0.4 | 0.41 |
| | — | 100 | — | 5 | <1 | 0.2 | 1.2 |
| | — | 50 | — | 5 | 0.5 | 0.2 | 0.7 |
| | — | 25 | — | 5 | 0.25 | 0.2 | 0.45 |
| | — | — | 25 | — | — | — | — |
| Chlorella sp. | 2 | — | — | — | — | — | — |
| | — | 1 | — | 0.5 | 0.5 | 0.5 | 1 |
| | — | — | 1 | — | — | — | — |

Note: Combinations of dodecylmorpholine acetate and dodecylamine acetate were not synergistic against *Aspergillus niger*.

Other embodiments of the present invention wil be apparent to those skilled in the art from consideration of the specification and practice of the invention disclosed herein. It is intended that the specification and examples be considered as exemplary only, with a true scope and spirit of the invention being indicated by Lne following claims.

What is claimed is:

1. A composition comprising (a) dodecylmorpholine or a salt thereof and (b) dodecylamine or a salt thereof, wherein components (a) and (b) are present in a synergistically microbically effective combined amount to control the growth of at least one microorganism.

2. The composition of claim 1, wherein the salt of dodecylmorpholine is dodecylmorpholine acetate, dodecylmorpholine propionate, a lauric salt of dodecylmorpholine, or a neodecanoic acid salt of dodecylmorpholine.

3. The composition of claim 1, wherein a salt of dodecylamine is dodecylamine acetate, dodecylamine propionate, a lauric salt of dodecylamine, or a neodecanoic salt of dodecylamine.

4. The composition of claim 1, wherein the microorganism is selected from bacteria, fungi, algae, or mixtures thereof.

5. The composition of claim 4, wherein said microorganism is *Pseudomonas aeruginosa, Enterobacter aerogenes, Aspergillus niger*, or Chlorella sp.

6. The composition of claim 1, wherein the weight ratio of (a) to (b) is from about 1:99 to about 99:1.

7. The composition of claim 6, wherein the weight ratio of (a) to (b) is from about 1:30 to about 30:1.

8. The composition of claim 6, wherein the weight ratio of (a) to (b) is from about 1:5 to about 5:1.

9. The composition of claim 1, wherein the weight ratio of concentrations are from about 0.01 to about 5000 ppm of dodecylmorpholine or a salt thereof and from about 0.01 to about 5000 ppm of dodecylamine or a salt thereof.

10. The composition of claim 9, wherein the said weight ratio of concentrations are from about 0.1 to about 2000 ppm dodecylmorpholine or a salt thereof and from about 0.1 to about 2000 ppm dodecylamine or a salt thereof.

11. The composition of claim 9, wherein the said weight ratio of concentrations are from about 0.1 to about 1000 ppm of dodecylmorpholine or a salt thereof and from about 0.1 to about 1000 ppm of dodecylamine or a salt thereof.

12. The composition of claim 1 wherein said composition consists essentially of components (a) and (b).

13. A method on making the composition of claim 1, comprising combining (a) dodecylmorpholine or a salt thereof with (b) dodecylamine or a salt thereof wherein components (a) and (b) are present in a synergistically microbicidally effective combined amount to control the growth of at least one microorganism.

14. A surface active agent comprising a mixture of (a) dodecylmorpholine or a salt thereof and (b) dodecylamine or a salt thereof, wherein (a) and (b) are present in combined synergistic amounts to control the growth of at least one bacteria, fungi, or algae.

15. A method of controlling the growth of at least one microorganism in or on a product, material, or medium susceptible to attack by said microorganism, comprising the step of adding to the said product, material, or medium, a composition comprising synergistic microbiocidal combined effective amounts of (a) dodecylmorpholine or a salt thereof and (b) dodecylamine or a salt thereof.

16. The method of claim 15, wherein salt of dodecylmorpholine is dodecylmorpholine acetate, dodecylmorpholine propionate, a lauric acid salt of dodecylmorpholine, or a neodecanoic acid salt of dodecylmorpholine.

17. The method of claim 15, wherein a salt of dodecylamine is dodecylamine acetate, dodecylamine propionate, a lauric salt of dodecylamine, or a neodecanoic salt of dodecylamine.

18. The method of claim 15, wherein said microorganism is selected from bacteria, fungi, algae.

19. The method of claim 15, wherein said microorganism is *Pseudomonas aeruginosa, Enterobacter aerogenes, Aspergillus niger*, or Chlorella sp.

20. The method of claim 15, wherein said product, material, or medium is wood pulp, wood chips, lumber, an adhesive, a coating, an animal hide, a paper mill liquor, a pharmaceutical formulation, a cosmetic, a toiletry formulation, a geological drilling lubricant, a petrochemical, paint, leather, wood, a metalworking fluid, cooling tower water, a tanning liquor, starch, a proteinaceous material, an acrylic latex paint emulsion, a textile, influent water, recreational water, waste water, a pasteurizer, a retort cooker, a lithographic fountain solution, or agricultural crop or seeds.

21. The method of claim 15, wherein said composition is in the form of a solid, dispersion, emulsion, or solution.

22. The method of claim 15, wherein said components (a) and (b) are added separately to the product, material, or medium.

23. The method of claim 15, wherein said components (a) and (b) are first combined and then added to the product, material, or medium.

24. The method of claim 15, wherein the weight ratio of concentrations is from about 0.01 to about 5000 ppm of dodecylmorpholine or a salt thereof, and from about 0.01 to about 5000 ppm of dodecylamine or a salt thereof.

25. The method of claim 24, wherein the weight ratio of concentrations is from about 0.1 to about 1000 ppm of dodecylmorpholine or a salt thereof, and from about 0.1 to about 1000 ppm dodecylamine or a salt thereof.

26. A method for preventing spoilage of a product, material, or medium, caused by bacteria, fungi, algae, or a mixture thereof, comprising the step of applying to said product, material, or medium, a composition comprising a) dodecylmorpholine or dodecylmorpholine acetate, and b) a dodecylamine or dodecylamine acetate, wherein said composition is added in synergistically effective amounts to prevent said spoilage.

27. The method of claim 21, wherein said product, material, or medium, is a seed or crops.

28. The method of claim 15, wherein said composition consists essentially of components (a) and (b).

* * * * *

UNITED STATES PATENT AND TRADEMARK OFFICE
CERTIFICATE OF CORRECTION

PATENT NO.: 5,929,073
DATED : July 27, 1999
INVENTORS: David OPPONG, Percy A. JAQUESS, Fernando Del CORRAL, and Marilyn S. WHITTEMORE It is certified that error appears in the above-identified patent and that said Letters Patent is hereby corrected as shown below:

IN THE CLAIMS

In claim 16, Column 9, line 40, before "salt" insert --the--.

In claim 18, Column 10, line 2, before "algae" insert --or--.

On the title page, item [54], after "DODECYLMORPHOLINE", INSERT --OR--.

Signed and Sealed this
First Day of February, 2000

Attest:

Attesting Officer

Q. TODD DICKINSON
Acting Commissioner of Patents and Trademarks